US011757101B2

(12) United States Patent
Numata et al.

(10) Patent No.: US 11,757,101 B2
(45) Date of Patent: *Sep. 12, 2023

(54) METAL POROUS BODY AND METHOD FOR PRODUCING METAL POROUS BODY

(71) Applicant: Sumitomo Electric Industries, Ltd., Osaka (JP)

(72) Inventors: Koma Numata, Osaka (JP); Masatoshi Majima, Osaka (JP); Tomoyuki Awazu, Osaka (JP); Mitsuyasu Ogawa, Osaka (JP); Takahiro Higashino, Osaka (JP); Hiromasa Tawarayama, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 339 days.

This patent is subject to a terminal disclaimer.

(21) Appl. No.: 16/500,981

(22) PCT Filed: Mar. 13, 2018

(86) PCT No.: PCT/JP2018/009740
§ 371 (c)(1),
(2) Date: Oct. 4, 2019

(87) PCT Pub. No.: WO2018/216321
PCT Pub. Date: Nov. 29, 2018

(65) Prior Publication Data
US 2020/0036011 A1   Jan. 30, 2020

(30) Foreign Application Priority Data

May 22, 2017 (JP) ................................. 2017-100734

(51) Int. Cl.
*H01M 4/02* (2006.01)
*H01M 4/86* (2006.01)
(Continued)

(52) U.S. Cl.
CPC ............. *H01M 4/8621* (2013.01); *A61C 7/20* (2013.01); *A61K 6/70* (2020.01); *A61L 27/06* (2013.01);
(Continued)

(58) Field of Classification Search
CPC .. H01M 4/8621; H01M 4/8626; H01M 4/861; H01M 4/8605; H01M 4/8636;
(Continued)

(56) References Cited

U.S. PATENT DOCUMENTS 4,483,752 A   11/1984 Kline
9,314,996 B1   4/2016 Wedding et al.
(Continued)

FOREIGN PATENT DOCUMENTS

CN   103320822 A   9/2013
CN   106460216 A   2/2017
(Continued)

OTHER PUBLICATIONS

Abstractor JP 2013-11003, Awazu et al., "Recovery Of Lithium Used For Lithium Cell, Involves Immersing Electrode In Lithium-containing Aqueous Solution, Adsorbing Lithium By Applying Voltage To Electrode, And Desorbing Lithium From Adsorption Agent By Applying Voltage", Jan. 17, 2013.*
(Continued)

*Primary Examiner* — Raymond Alejandro
(74) *Attorney, Agent, or Firm* — Faegre Drinker Biddle & Reath LLP

(57) ABSTRACT

The metal porous body having a framework of a three-dimensional network structure is disclosed. The framework is formed of a metal film, the framework has an interior that is hollow, and the metal film contains titanium metal or titanium alloy as a main component.

26 Claims, 7 Drawing Sheets

(51) Int. Cl.

| | | |
|---|---|---|
| A61K 6/70 | (2020.01) | |
| A61C 7/20 | (2006.01) | |
| A61L 27/06 | (2006.01) | |
| A61L 27/56 | (2006.01) | |
| A61L 31/02 | (2006.01) | |
| A61L 31/14 | (2006.01) | |
| C25B 1/04 | (2021.01) | |
| C25D 1/08 | (2006.01) | |
| C25D 3/66 | (2006.01) | |
| H01M 8/0232 | (2016.01) | |
| H01M 8/0245 | (2016.01) | |
| C25B 11/031 | (2021.01) | |

(52) U.S. Cl.
CPC ............ *A61L 27/56* (2013.01); *A61L 31/022* (2013.01); *A61L 31/146* (2013.01); *C25B 1/04* (2013.01); *C25B 11/031* (2021.01); *C25D 1/08* (2013.01); *C25D 3/66* (2013.01); *H01M 8/0232* (2013.01); *H01M 8/0245* (2013.01); *A61L 2430/20* (2013.01); *A61L 2430/24* (2013.01); *A61L 2430/38* (2013.01); *H01M 2004/8689* (2013.01)

(58) Field of Classification Search
CPC ............ H01M 8/0232; H01M 8/0245; H01M 2004/8689; A61K 6/70; C25B 11/031; C25B 1/04; A61C 7/20; A61L 27/06; A61L 27/56; A61L 2430/20; A61L 2430/24; A61L 2430/38; A61L 31/022; A61L 31/146; C25D 1/08; C25D 3/66
See application file for complete search history.

(56) References Cited

U.S. PATENT DOCUMENTS

| | | | | |
|---|---|---|---|---|
| 2003/0153981 A1* | 8/2003 | Wang | ............... | B22F 3/114 623/22.21 |
| 2007/0150068 A1 | 6/2007 | Dong et al. | | |
| 2012/0199488 A1 | 8/2012 | Parker et al. | | |
| 2017/0121835 A1* | 5/2017 | Goto | ............... | C25D 1/08 |

FOREIGN PATENT DOCUMENTS

| | | | | |
|---|---|---|---|---|
| EP | 3633075 A1 | 4/2020 | | |
| EP | 3633079 A1 | 4/2020 | | |
| JP | H06-212323 A | 8/1994 | | |
| JP | H08-225980 A | 9/1996 | | |
| JP | H09-71890 A | 3/1997 | | |
| JP | 2013-11003 | * | 1/2013 | ............... C25B 1/14 |
| JP | 2013-11003 A | 1/2013 | | |
| JP | 2013-133504 A | 7/2013 | | |
| JP | 2014-91151 A | 5/2014 | | |
| JP | 2015-193899 A | 11/2015 | | |
| JP | 2017-54797 A | 3/2017 | | |

OTHER PUBLICATIONS

CN Office Action dated Feb. 25, 2021 in Chinese Application No. 201880026223.1 (with attached English-language translation).
Robin A. et al., "Electrolytic Coating of Titanium Onto Iron and Nickel Electrodes in the Molten LiF+NaF+KF Eutectic", Journal of Electroanalytical Chemistry, 230 (1987), pp. 126-127, 137, 140.
Zhang Zhaoxian et al., "Titanium Electrode Reaction Engineering", pp. 305-307, Beijing: Metallurgical Industry Press, Apr. 30, 2009.
Li Jingyuan et al., "Special Metal Materials and Processing Technology", pp. 255-259, Beijing: Metallurgical Industry Press, May 31, 2010.
Tiechui Yuan et al., "Preparation of High-purity Titanium by Molten-salt Electrolysis Process," Advanced Materials Research, vols. 284-286 (2011), pp. 1477-1482.
Lianxun Song et al., "Electrochemical behaviors of Ti(III) in molten NaCl—KCl under various contents of fluoride," Electrochimica Acta 256 (2017), pp. 252-258.
Office Action dated Feb. 17, 2021 that issued in U.S. Appl. No. 16/605,960.
Numata, Koma, et al., "Composite Metal Porous Body and Method for Producing Composite Metal Porous Body," U.S. Appl. No. 16/605,960, filed Oct. 17, 2019, including as-filed specification, claims, abstract and drawings, 64 pages.
Office Action dated Jul. 24, 2020 that issued in U.S. Appl. No. 16/085,725.
Office Action dated Aug. 23, 2021 that issued in U.S. Appl. No. 16/605,960.
Office Action dated Feb. 17, 2022 that issued in U.S. Appl. No. 16/605,960.
Office Action dated Apr. 20, 2022 that issued in U.S. Appl. No. 16/605,960.

* cited by examiner

CORROSION RESISTANCE TO SALINE
(0.9wt%/vol NaCl AQUEOUS SOLUTION @1V)

SIMULATED SEAWATER
(3.4% NaCl AQUEOUS SOLUTION)

METAL POROUS BODY AND METHOD FOR PRODUCING METAL POROUS BODY

TECHNICAL FIELD

The present disclosure relates to a metal porous body and a method for producing the metal porous body. The present application claims the benefit of priority to Japanese Patent Application No. 2017-100734 filed on May 22, 2017, the entire contents of which are incorporated herein by reference.

BACKGROUND ART

Titanium is a metal excellent in corrosion resistance, heat resistance and specific strength. However, titanium is costly to produce and difficult to smelt and machine, which hinders the widespread use of titanium. At present, dry deposition, such as chemical vapor deposition (CVD) and physical vapor deposition (PVD), is being used in industry as one of the methods that take advantage of high corrosion resistance, high strength, and other properties of titanium and titanium compounds. Such dry deposition, however, cannot be applied to a complex-shaped base material. As a method for depositing titanium so as to solve the problem, the electrodeposition of titanium in a molten salt may be used.

For example, Japanese Patent Laying-Open No. 2015-193899 (PTL 1) describes that an alloy film of Fe and Ti is formed on the surface of a Fe wire by using a molten salt bath of KF—KCl added with $K_2TiF_6$ and $TiO_2$.

There is also known a smelting method for precipitating high-purity titanium metal on a base material by using a molten salt bath. For example, Japanese Patent Laying-Open No. 08-225980 (PTL 2) describes a method for precipitating high-purity titanium on the surface of nickel by using a NaCl bath added with $TiCl_4$ as the molten salt bath. Further, Japanese Patent Laying-Open No. 09-071890 (PTL 3) describes a method for precipitating high-purity titanium on the surface of a titanium bar by using a NaCl bath or a Na—KCl bath.

CITATION LIST

Patent Literature

PTL 1: Japanese Patent Laying-Open No. 2015-193899
PTL 2: Japanese Patent Laying-Open No. 08-225980
PTL 3: Japanese Patent Laying-Open No. 09-071890

SUMMARY OF INVENTION

The metal porous body according to one aspect of the present invention is a metal porous body having a framework of a three-dimensional network structure. The framework is hollow inside and is formed of a metal film, and the metal film contains titanium metal or titanium alloy as the main component.

The method for producing a metal porous body according to one aspect of the present invention is for producing the metal porous body according to one aspect of the present invention. The method includes: a molten salt bath preparation step of preparing a molten salt bath that contains an alkali metal halide and a titanium compound; a dissolution step of dissolving titanium metal in the molten salt bath; an electrolysis step of performing a molten salt electrolysis by using a cathode and an anode provided in the molten salt bath in which the titanium metal is dissolved so as to electrodeposit the titanium metal on the surface of the cathode; and a treatment step of treating the cathode on which the titanium metal is electrodeposited with an acid or an alkali. In the dissolution step, the titanium metal is supplied in at least a minimum amount required to convert $Ti^{4+}$ in the molten salt bath into $Ti^{3+}$ by a comproportionation reaction represented by the following formula (1):

in the electrolysis step, a porous base material which has a three-dimensional network structure is used as the cathode.

DETAILED DESCRIPTION

Figure 1:
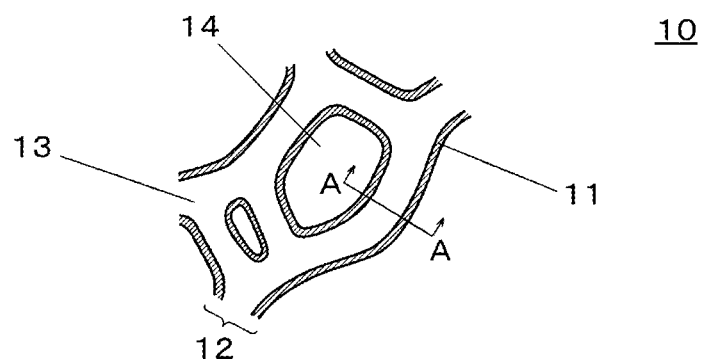
FIG. 1 is an enlarged view schematically illustrating a partial cross section of an example metal porous body according to an embodiment of the present invention.

Problem to be Solved by the Present Disclosure

According to the results of studies conducted by the inventors of the present invention, although a Fe—Ti alloy film can be electrodeposited by the method described in PTL 1, a titanium metal film cannot be electrodeposited by the method. The reason is that the Fe—Ti alloy film is stable in the molten salt bath, whereas Ti metal will dissolve in the molten salt bath by a comproportionation reaction.

The methods described in PTL 2 and PTL 3, on the other hand, are not for plating but for smelting titanium metal. In other words, The titanium electrodeposited by the methods described in PTL 2 and PTL 3 is in the form of a dendrite, which makes it impossible to provide a smooth titanium film.

Furthermore, when titanium metal is used as an insoluble positive electrode in the production of hydrogen, for example, the reaction area may be increased by using titanium metal having a large surface area so as to reduce electrical resistance. In order to produce titanium metal having a large surface area, for example, a possible approach is to use a base material that has a large surface area and plate titanium metal on the surface of the base material. As examples of a base material that has a large surface area, a metal porous body having a framework of a three-dimensional network structure may be given, but a method for plating titanium metal on the surface of a base material having such an extremely complicated three-dimensional shape has not been developed.

In view of the above problems, an object of the present invention is to provide a metal porous body which is a titanium-plated product and has a large surface area as compared with flat titanium metal, and a method for producing the metal porous body.

Advantageous Effect of the Present Disclosure

According to the present invention, it is possible to provide a metal porous body which is a titanium-plated product and has a larger surface area than flat titanium metal, and a method for producing the metal porous body.

DESCRIPTION OF EMBODIMENTS

First, embodiments of the present disclosure are enumerated hereinafter.

(1) The metal porous body according to an embodiment of the present invention is a metal porous body having a framework of a three-dimensional network structure. The framework is hollow inside and is formed of a metal film, and the metal film contains titanium metal or titanium alloy as the main component.

In the metal porous body according to an embodiment of the present invention, the expression that "having titanium metal or titanium alloy as the main component" or "containing titanium metal or titanium alloy as the main component" means that the greatest component contained in the metal film (framework) is titanium metal or titanium alloy.

According to the embodiment of the present invention described in the above (1), the metal porous body which is a titanium-plated product may have a larger surface area than flat titanium.

(2) In the metal porous body described in the above (1), it is preferable that the metal film has an average thickness of 1 µm or more and 300 µm or less.

According to the embodiment of the present invention described in the above (2), the metal porous body may be made higher in corrosion resistance.

(3) It is preferable that the metal porous body according to the above (1) or (2) has a porosity of 60% or more and 98% or less.

According to the embodiment of the present invention described in the above (3), the metal porous body may be made lighter in weight.

(4) It is preferable that the metal porous body according to any one of the above (1) to (3) has an average pore diameter of 50 µm or more and 5000 µm or less.

According to the embodiment of the present invention described in the above (4), the metal porous body may be made excellent in bending property and strength. In addition, when the metal porous body is used as an electrode of a battery or in water electrolysis or the like, the electrolytic solution is easy to infiltrate into the metal porous body so as to increase the reaction area, which makes it possible to reduce the electrical resistance.

(5) It is preferable that the metal porous body according to any one of the above (1) to (3) has an outer profile of a sheet shape, and the average pore diameter is different between a region on one side and a region on the other side in the thickness direction of the sheet.

(6) It is preferable that the metal porous body according to any one of the above (1) to (3) and (5) has an outer profile of a sheet shape, and the apparent weight is different between a region on one side and a region on the other side in the thickness direction of the sheet.

According to the embodiment of the present invention described in the above (5) or (6), it is difficult for a crack to occur in the framework when the metal porous body is bent.

(7) It is preferable that the metal porous body according to any one of the above (1) to (3) has an outer profile of a sheet shape, and the average pore diameter is different between the region of a central region and an outer region located outside the central region in the thickness direction of the sheet.

(8) It is preferable that the metal porous body according to any one of the above (1) to (3) and (7) has an outer profile of a sheet shape, and the apparent weight is different between a central region and an outer region located outside the central region in the thickness direction of the sheet.

The central region of a metal porous body is defined in such a manner that when the metal porous body is divided into three divisions (for example, substantially three equal divisions) in the thickness direction (the thickness direction of the sheet), the central region is the central division sandwiched by the two divisions at both sides. Further, the outer region located outside the central region of the metal porous body is defined in such a manner that when the metal porous body is divided into three divisions (for example, substantially three equal divisions) in the thickness direction (the thickness direction of the sheet), the outer region located outside the central region is any one of the two divisions at both sides.

According to the embodiment of the present invention described in the above (7) or (8), the metal porous body may be suitably used as an electrolytic electrode and an insoluble positive electrode. However, the pore diameter and the apparent weight are not necessarily limited to change in three equal regions, and it is acceptable that the central region is thick while the outer region is thin, or it is acceptable that the central region is thin while the outer region is thick.

(9) A method for producing a metal porous body according to an embodiment of the present invention is a method for manufacturing the metal porous body according to the above (1). The method includes: a molten salt bath preparation step of preparing a molten salt bath that contains an alkali metal halide and a titanium compound; a dissolution step of dissolving titanium metal in the molten salt bath; an electrolysis step of performing a molten salt electrolysis by using a cathode and an anode provided in the molten salt bath in which the titanium metal is dissolved so as to electrodeposit the titanium metal on the surface of the cathode; and a treatment step of treating the cathode on which the titanium metal is electrodeposited with an acid or an alkali. In the dissolution step, the titanium metal is supplied in at least a minimum amount required to convert $Ti^{4+}$ in the molten salt bath into $Ti^{3+}$ by a comproportionation reaction represented by the following formula (1):

$$3Ti^{4+} + Ti\ metal \rightarrow 4Ti^{3+} \qquad (1),$$

and in the electrolysis step, a porous base material which has a three-dimensional network structure is used as the cathode.

According to the embodiment of the present invention described in the above (9), it is possible for the method to produce a metal porous body which is a titanium-plated product and has a larger surface area than flat titanium.

(10) In the method for producing a metal porous body described in the above (9), it is preferable that the porous base material includes at least one material selected from the group consisting of a metal, an alloy, a carbon material and a conductive ceramic.

According to the embodiment of the present invention described in the above (10), the porous base material used in the electrolysis step may be prepared relatively easily.

(11) The method for producing a metal porous body according to (9) or (10) above, it is preferable that the treatment step is performed at a temperature of 20° C. or more.

According to the embodiment of the present invention described in the above (11), the porous base material may be easily removed in the treatment step.

(12) In the method for producing a metal porous body according to any one of the above (9) to (11), it is preferable that the porous base material used as the cathode has an outer profile of a sheet shape, and the average pore diameter is different between a region on one side and a region on the other side in the thickness direction of the sheet, or it is preferable that the porous base material used as the cathode has an outer profile of a sheet shape, and the average pore diameter is different between a central region and an outer region located outside the central region in the thickness direction of the sheet.

According to the embodiment of the present invention described in the above (12), it is possible for the method to produce a metal porous body according to any one of the above (5) to (8).

(13) In the method for producing a metal porous body according to any one of the above (9) to (12), it is preferable that the titanium metal to be dissolved in the dissolution step is a titanium sponge.

According to the embodiment of the present invention described in the above (13), it is possible to promote the comproportionation reaction of titanium in the dissolution step.

Note that the titanium sponge refers to a porous titanium metal having a porosity of 1% or more. The porosity of a titanium sponge is calculated by the following formula:

100−(the volume calculated from the mass)/(the apparent volume)×100.

(14) In the method for producing a metal porous body according to any one of the above (9) to (13), it is preferable that the titanium metal is used as the anode.

According to the embodiment of the present invention described in the above (14), it is possible to stably and continuously electrodeposit the titanium metal film on the surface of the framework of the porous base material which is used as the cathode.

(15) An insoluble positive electrode according to an embodiment of the present invention is made of the metal porous body described in any one of the above (1) to (8).

(16) It is preferable that the insoluble positive electrode described in the above (15) is used in the production of hydrogen.

According to the embodiments of the present invention described in the above (15) and (16), the insoluble positive electrode may be made low in electrical resistance.

(17) The fuel-cell electrode according to an embodiment of the present invention is made of the metal porous body according to any one of the above (1) to (8).

(18) It is preferable that the fuel-cell electrode described in the above (17) is used in a polymer electrolyte fuel cell.

According to the embodiments of the present invention described in the above (17) and (18), the fuel-cell electrode may be made to have a high porosity and a satisfactory electrical conductivity.

(19) A method for producing hydrogen according to an embodiment of the present invention is used to generate hydrogen by electrolyzing water using the metal porous body according to any one of the above (1) to (8) as an electrode.

According to the embodiment of the present invention described in the above (19), since the contact area between water and the electrode is increased, it is possible to improve the efficiency of water electrolysis.

(20) In the above production method, it is preferable that the water is an alkaline aqueous solution.

According to the embodiment of the present invention described in the above (20), since the electrolysis may be conducted at a lower voltage, it is possible to produce hydrogen at a lower power consumption.

(21) In the method for producing hydrogen according to the above (19) or (20), it is preferable that the metal porous bodies are disposed at both sides of a solid polymer electrolyte membrane and configured to be in contact with the solid polymer electrolyte membrane so that the metal porous bodies act as a positive electrode and a negative electrode, respectively, so as to electrolyze water supplied to the positive electrode side so as to generate hydrogen at the negative electrode side.

According to the embodiment of the present invention described in the above (21), it is possible to produce hydrogen with a high purity.

(22) A hydrogen producing apparatus according to an embodiment of the present invention is configured to generate hydrogen by electrolyzing water, and includes the metal porous body according to any one of the above (1) to (8) as an electrode.

According to the embodiment of the present invention described in the above (22), since the contact area between water and the electrode is increased, it is possible for the hydrogen producing apparatus to improve the efficiency of water electrolysis.

(23) In the hydrogen producing apparatus describe in the above (22), it is preferable that the water is a strong alkaline aqueous solution.

According to the embodiment of the present invention described in the above (23), since the electrolysis may be conducted at a lower voltage, it is possible for the hydrogen producing apparatus to produce hydrogen at a lower power consumption.

(24) The hydrogen producing apparatus described in the above (22) or (23) includes a positive electrode and a negative electrode disposed at both sides of a solid polymer electrolyte membrane and configured to be in contact with the solid polymer electrolyte membrane. The hydrogen producing apparatus is configured to electrolyze water supplied to the positive electrode side so as to generate hydrogen at the negative electrode side, and at least one of the positive electrode and the negative electrode is preferably made of the metal porous body.

According to the embodiment of the present invention described in the above (24), it is possible for the hydrogen producing apparatus to produce hydrogen with a high purity.

(25) A biomaterial according to an embodiment of the present invention is made of the metal porous body according to any one of the above (1) to (8).

According to the embodiment of the present invention described in the above (25), the biomaterial may be made excellent in corrosion resistance.

(26) A medical device according to an embodiment of the present invention includes the biomaterial according to the above (25).

(27) It is preferable that the medical device according to the above (26) is selected from the group consisting of a spinal fixation device, a fracture fixation member, an artificial joint, an artificial valve, an intravascular stent, a dental plate, an artificial tooth root and an orthodontic wire.

According to the embodiments of the present invention described in the above (26) and (27), the medical device may be made excellent in corrosion resistance.

DETAILS OF EMBODIMENT

Specific examples of the metal porous body and the method for producing the same according to an embodiment of the present invention will be described hereinafter in more detail. Note that the present embodiment is not limited to the description but is defined by the terms of the claims. It is intended that the present embodiment encompasses any modification within the meaning and scope equivalent to the terms of the claims. In the present specification, the expression in the form of "A to B" refers to an upper limit and a lower limit of a range (in other words, A or more and B or less), and if A is described without a unit but B is described with a unit, then A has the same unit as B.

<Metal Porous Body>

The metal porous body according to an embodiment of the present invention has a framework of a three-dimensional network structure. The "three-dimensional network structure" refers to a structure in which solid components (such as metals, resins or the like) construct a three-dimensional network. The metal porous body as a whole may have a sheet shape, a rectangular shape, a spherical shape, or a cylindrical shape, for example. In other words, the metal porous body may have an outer profile of a sheet shape, a rectangular shape, a spherical shape, or a cylindrical shape.

FIG. 1 is an enlarged view schematically illustrating a cross section of an example metal porous body according to an embodiment of the present invention. As illustrated in FIG. 1, in a metal porous body 10, a framework 12 is formed of a metal film 11 (hereinafter may be referred to as "titanium metal film 11" where appropriate). An interior 13 of the framework 12 is hollow. The metal porous body 10 contains pores that are communicating with each other, and each pore 14 is formed by the framework 12.

The titanium metal film 11 contains titanium metal or titanium alloy as the main component. The titanium metal film 11 may contain a metals or an alloy other than titanium as long as the content of titanium is 90 mass % or more. Examples of other metals or alloys may include nickel, aluminum, copper, tungsten, molybdenum, chromium and tin, or an alloy thereof. It is preferable that the content of titanium in the titanium metal film 11 is as high as possible. The content of titanium in the titanium metal film 11 constituting the framework 12 of the metal porous body 10 is preferably 93 mass % or more, and more preferably 95 mass % or more. Although the upper limit of the content of titanium is not particularly limited, it may be 100 mass % or less, for example.

In the metal porous body according to an embodiment of the present invention, the average film thickness (the average thickness) of the metal film (for example, the titanium metal film formed on the surface of the framework) is preferably 1 µm or more and 300 µm or less. When the average thickness of the metal film (for example, the average film thickness of the titanium metal film) is 1 µm or more, the corrosion resistance of the framework of the metal porous body may be improved sufficiently. On the other hand, from the viewpoint of manufacturing cost, the average thickness of the metal film is preferably about 300 µm or less. The average thickness of the metal film is more preferably 5 µm or more and 100 µm or less, further more preferably 10 µm or more and 50 µm or less, and even more preferably 15 µm or more and 50 µm or less.

The average thickness of the metal film is measured by observing a cross section of the metal porous body with an electron microscope as follows. As a specific example, a method for measuring the average film thickness of the titanium metal film is schematically illustrated in FIGS. 2 to 6.

Figure 2:
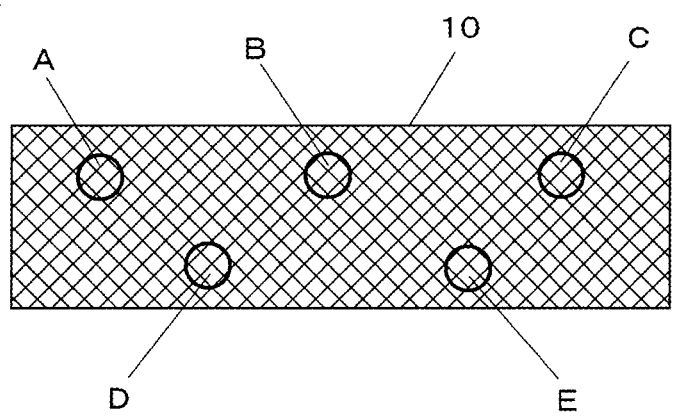
FIG. 2 is a schematic view illustrating areas A to E that are defined on a sheet-shaped metal porous body in a method for measuring an average film thickness of a metal film (titanium metal film) on the metal porous body.
Figure 3:
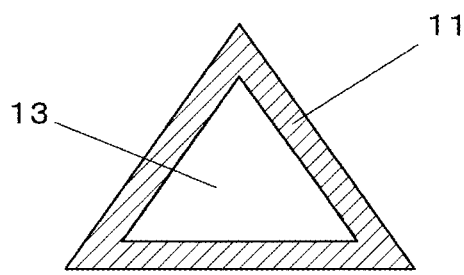
FIG. 3 is a schematic view illustrating a photograph when a cross section (cross section taken along line A-A in FIG. 1) of a framework in area A of the metal porous body in FIG. 2 is observed with a scanning electron microscope.

First, as illustrated in FIG. 2, the metal porous body 10 in the form of a sheet is arbitrarily divided into areas, and 5 areas (area A to area E) are selected as measurement spots. Then, one framework of the metal porous body is arbitrarily selected from each area, and the cross section taken along line A-A (hereinafter referred to as "A-A cross section") of the framework as illustrated in FIG. 1 is observed with a scanning electron microscope (SEM). The A-A cross section of the framework of the metal porous body is schematically illustrated in FIG. 3. As illustrated in FIG. 3, in the A-A cross section of the framework, the framework formed by the titanium metal film 11 has a substantially triangular shape, and the interior 13 of the framework is hollow. In another aspect, the A-A cross section of the framework may be circular or quadrilateral, and the interior 13 of the framework is hollow.

When it is possible to observe the entire A-A cross section of the framework by SEM, the magnification power is further increased in such a manner that the entire titanium metal film 11 in the thickness direction can be observed and the thickness can be observed as large as possible in one field of view. Then, the same A-A cross section of the framework is observed at different fields of view so as to determine the maximum thickness and the minimum thickness of the titanium metal film 11 in 3 fields of view. For all of the 5 areas, the maximum thickness and the minimum thickness of the titanium metal film are measured for the A-A cross section of one arbitrary framework in 3 fields of view, and the averaged value is defined as the average thickness of the titanium metal film.

Figure 4:
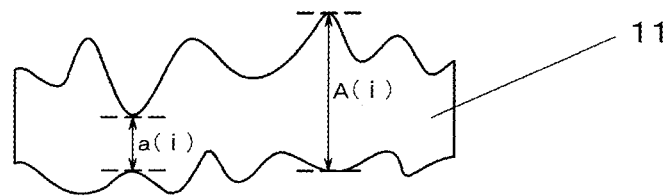
FIG. 4 is a schematic view illustrating an example field of view (i) when a metal film 11 (titanium metal film 11) illustrated in FIG. 3 is magnified and observed with a scanning electron microscope.
Figure 5:
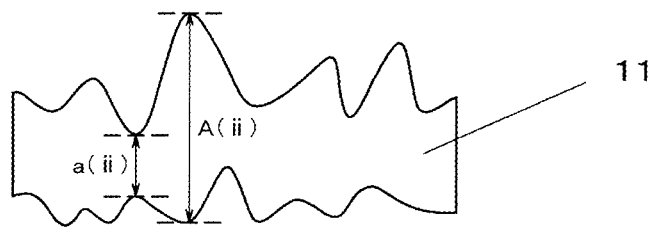
FIG. 5 is a schematic view illustrating an example field of view (ii) when the metal film 11 (titanium metal film 11) illustrated in FIG. 3 is magnified and observed with a scanning electron microscope.
Figure 6:
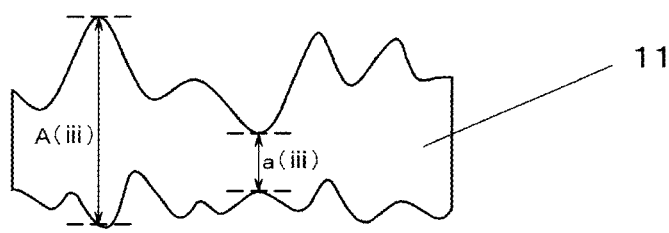
FIG. 6 is a schematic view illustrating an example field of view (iii) when the metal film 11 (titanium metal film 11) illustrated in FIG. 3 is magnified and observed with a scanning electron microscope.

As an example, FIG. 4 illustrates a conceptual diagram of a field of view (i) obtained when the A-A cross section of any one framework is observed by SEM in the area A of the metal porous body 10 as illustrated in FIG. 2. Similarly, FIG. 5 illustrates a conceptual diagram of a field of view (ii) of the A-A cross section of the same framework, and FIG. 6 illustrates a conceptual diagram of a field of view (iii).

In each of the fields of view (i) to (iii) obtained when the A-A cross section of any one framework of the titanium metal film 11 is observed by SEM in the area A, the greatest thickness of the titanium metal film 11 (the maximum thickness A(i), the maximum thickness A(ii) and the maximum thickness A(iii)), and the smallest thickness of the titanium metal film 11 (the minimum thickness a(i), the minimum thickness a(ii) and the minimum thickness a(iii)) are measured. When a titanium alloy layer is formed on a surface of the titanium metal film 11 facing the interior 13 of the framework, the thickness of the titanium metal film 11 is defined as the sum of the thickness of the titanium alloy layer and thickness of the titanium metal film 11. Thereby, the maximum thickness A(i) to A(iii) and the minimum thickness a(i) to a(iii) in 3 fields of view for the A-A cross section of any one framework are measured for the area A. Similarly, the maximum thickness and the minimum thickness of the titanium metal film 11 in 3 fields of view are measured for each of the areas B, C, D and E in the same manner as the area A.

The average value of the maximum thickness A(i) to the maximum thickness E(iii) and the minimum thickness a(i) to the minimum thickness e(iii) of the titanium metal film 11 measured as described above is defined as the average film thickness of the titanium metal film (in other words, the average thickness of the metal film).

The porosity of the metal porous body is preferably 60% or more and 98% or less. When the porosity of the metal porous body is 60% or more, the metal porous body may have a relatively light weight, and when the metal porous body is used as an electrode of a battery or in water electrolysis or the like, it is possible to increase the reaction area so as to reduce the electrical resistance. On the other hand, when the porosity of the metal porous body is 98% or less, the metal porous body may have a sufficient strength. From these viewpoints, the porosity of the metal porous body is more preferably 70% or more and 98% or less, further more preferably 80% or more and 98% or less, and even more preferably 80% or more and 96% or less.

The porosity of the metal porous body is defined by the following equation:

$$\text{porosity} = (1-(\text{mass of the porous body [g]}/(\text{volume of the porous body [cm}^3\text{]} \times \text{density of the material [g/cm}^3\text{]})) \times 100 \ [\%]$$

The average pore diameter of the metal porous body is preferably 50 μm or more and 5000 μm or less. When the average pore diameter is 50 μm or more, it is possible to increase the strength of the metal porous body. In addition, when the metal porous body is used as an electrode of a battery or in water electrolysis or the like, it is possible to increase the reaction area so as to reduce the electrical resistance. When the average pore diameter is 5000 μm or less, it is possible to improve the bending property of the metal porous body. From these viewpoints, the average pore diameter of the metal porous body is more preferably 100 μm or more and 500 μm or less, further more preferably 150 μm or more and 400 μm or less, and even more preferably 280 μm or more and 400 μm or less.

The average pore diameter of the metal porous body is defined in such a manner that while the surface of the metal porous body is being observed under a microscope or the like, the number of pores per inch (25.4 mm) is counted as the number of cells, and the average pore diameter is calculated as 25.4 mm/the number of cells.

When the metal porous body according to an embodiment of the present invention has an outer profile of a sheet shape, the thickness of the sheet is preferably 0.1 mm or more and 5 mm or less, and more preferably 0.3 mm or more and 1.5 mm or less. The thickness may be measured, for example, by using a digital thickness gauge.

Figure 7:
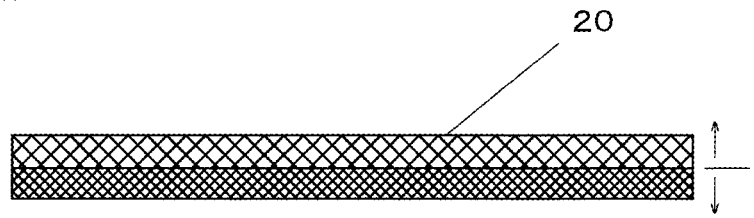
FIG. 7 is a diagram schematically illustrating an example metal porous body wherein the average pore diameter is different between a region above the center line and a region below the center line in the thickness direction.

It is preferable that the metal porous body according to an embodiment of the present invention has an outer profile of a sheet shape, and the average pore diameter is different between a region on one side and a region on the other side in the thickness direction of the sheet. In another aspect, it is acceptable that the metal porous body has an outer profile of a sheet shape and that the average pore diameter continuously changes from the region on one side toward the region on the other side in the thickness direction of the sheet. In another aspect, as illustrated in FIG. 7, it is preferable that the average pore diameter is different between a region above the center line and a region below the center line in the thickness direction of the sheet-shaped metal porous body 20. Note that the center line of a metal porous body refers to the boundary when the sheet is divided into 2 divisions (for example, substantially 2 equal divisions) in the thickness direction. As the average pore diameter becomes larger, it is easy for the metal porous body to undergo deformation such as bending or compression; as the average pore diameter becomes smaller, it is difficult for the metal porous body to undergo deformation. Therefore, for example, when a metal porous body having different average pore diameter between the region on one side and the region on the other side in the thickness direction (for example, the region above the center line and the region below the center line in the thickness direction) is bent so that the surface having a larger average pore diameter becomes the inner surface, it is difficult for a crack (fracture) to occur in the framework.

It is preferable that the metal porous body according to an embodiment of the present invention has an outer profile of a sheet shape, and the apparent weight is different between a region on one side and a region on the other side in the thickness direction of the sheet. In another aspect, it is acceptable that the metal porous body has an outer profile of a sheet shape, and the apparent weight continuously changes from the region on one side toward the region on the other side in the thickness direction of the sheet. In another aspect, it is preferable that the apparent weight is different between a region above the center line and a region below the center line in the thickness direction of the metal porous body. The apparent weight refers to the apparent mass per unit area on the main surface of the sheet-shaped metal porous body.

Figure 8:
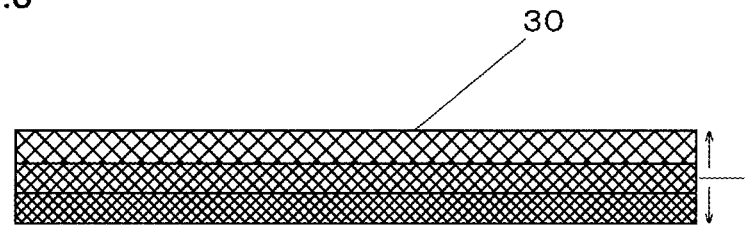
FIG. 8 is a diagram schematically illustrating another example metal porous body wherein the average pore diameter is different between the region above the center line and the region below the center line in the thickness direction.

As an example metal porous body having different apparent weight between a region above the center line and a region below the center line in the thickness direction of the metal porous body, the metal porous body 20 of which the average pore diameter is different between the region above the center line and the region below the center line in the thickness direction as illustrated in FIG. 7 or the metal porous body 30 of which the average pore diameter becomes smaller (or larger) from one surface of the metal porous body toward the other surface thereof as illustrated in FIG. 8 may be given. When the metal porous body 30 illustrated in FIG. 8 is bent so that the surface having a larger average pore diameter faces the inner side, it is difficult for a crack (fracture) to occur in the framework.

It is preferable that the metal porous body has an outer profile of a sheet shape, and the average pore diameter is different between a central region and an outer region located outside the central region in the thickness direction of the sheet.

Figure 9:
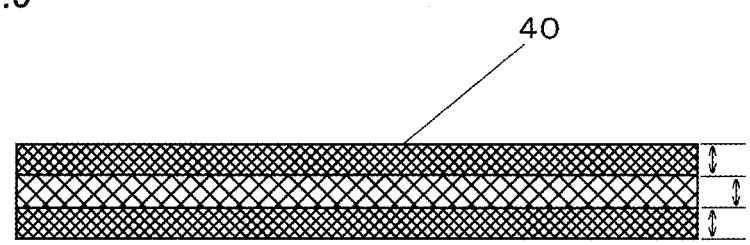
FIG. 9 is a diagram schematically illustrating an example metal porous body wherein the average pore diameter in a central region in the thickness direction is larger than the average pore diameter in an outer region located outside the central region in the thickness direction.

For example, as illustrated in FIG. 9, when the metal porous body 40 of which the average pore diameter in the central region is larger than the average pore diameter in an outer region located outside the central region in the thickness direction is used as an insoluble positive electrode, the reaction resistance to the electrolytic solution is reduced and the generated gas is difficult to escape, which makes it possible to reduce the overvoltage.

Figure 10:
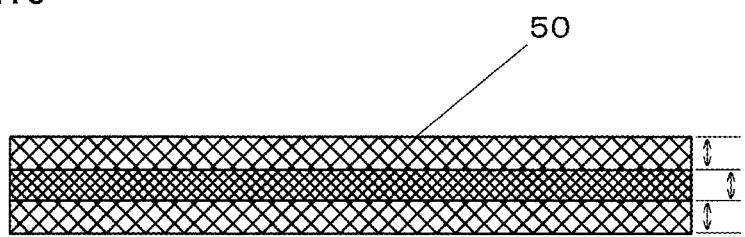
FIG. 10 is a diagram schematically illustrating an example metal porous body wherein the average pore diameter in a central region in the thickness direction is smaller than the average pore diameter in an outer region located outside the central region in the thickness direction.

In addition, as illustrated in FIG. 10, when the metal porous body 50 of which the average pore diameter in the central region is smaller than the average pore diameter in an outer region located outside the central region in the thickness direction is used as an electrolytic electrode, the electrolytic solution is easy to infiltrate into the interior of the metal porous body 50 in the thickness direction, and thereby the reaction area is increased, which makes it possible to reduce the electrical resistance.

In another aspect, the metal porous body may have an outer profile of a sheet shape, and the average pore diameter may change continuously from the central region toward an outer region located outside the central region in the thickness direction of the sheet.

It is preferable that the metal porous body has an outer profile of a sheet shape, and the apparent weight of the metal is different between a central region and an outer region located outside the central region in the thickness direction of the sheet. As examples of a metal porous body wherein the apparent weight of the metal is different between a central region and an outer region located outside the central region in the thickness direction of the sheet, as illustrated in FIG. 9 or FIG. 10, the metal porous body wherein the average pore diameter in the central region is different from the average pore diameter in an outer region located outside the central region in the thickness direction may be given.

For example, as illustrated in FIG. 9, when the metal porous body 40 wherein the apparent weight of the metal in the central region is smaller than the apparent weight of the metal in an outer region located outside the central region in the thickness direction in used as an insoluble positive electrode, the reaction resistance to the electrolytic solution is lowered and the generated gas is difficult to escape, which makes it possible to reduce the overvoltage.

In addition, as illustrated in FIG. 10, when the metal porous body 50 wherein the apparent weight of the metal in the central region is smaller than the apparent weight of the metal in an outer region located outside the central region in the thickness direction is used as an electrolytic electrode, the electrolytic solution is easy to infiltrate into the interior of the metal porous body 50 in the thickness direction, and thereby the reaction area is increased, which makes it possible to reduce the electrical resistance.

In another aspect, it is acceptable that the metal porous body has an outer profile of a sheet shape, and the apparent weight of the metal continuously changes from the central region toward an outer region located outside the central region in the thickness direction of the sheet.

<Method for Producing Metal Porous Body>

The method for producing a metal porous body according to an embodiment of the present invention is a method for producing the metal porous body according to the above-mentioned embodiment of the present invention. The method includes a molten salt bath preparation step, a dissolution step, an electrolysis step, and a treatment step. Each step will be described in detail hereinafter.

(Molten Salt Bath Preparation Step)

The molten salt bath preparation step is a step of preparing a molten salt bath that contains an alkali metal halide and a titanium compound. The term of "molten salt bath" refers to a plating bath using molten salt.

As examples of a molten salt containing an alkali metal halide, KF—KCl, LiF—LiCl, LiF—NaF, LiF—NaCl, and LiCl—NaF may be given.

KF—KCl eutectic molten salt has a lower melting point and is more soluble in water than the molten salt of KF alone or KCl alone. Therefore, when KF—KCl eutectic molten salt is used as a molten salt bath, the molten salt bath is excellent in water washability.

As examples of a titanium compound, $K_2TiF_6$, $TiCl_2$, $TiCl_3$ and $TiCl_4$ may be given.

For example, if a molten salt bath of KF—KCl eutectic molten salt with $K_2TiF_6$ added is used for Ti electroplating, it is possible to electrodeposit a titanium metal film which is a metal film on the surface of the framework of the porous base material which is used as the cathode.

The mixing ratio of KF and KCl may be appropriately changed according to required conditions, and the molar mixing ratio may be about 10:90 to 90:10. In another aspect, the molar mixing ratio of KF and KCl may be 10:90 to 45:55 or 45:55 to 90:10.

By adding a titanium compound such as $K_2TiF_6$ to the molten salt containing an alkali metal halide as mentioned above, the molten salt bath may be made possible to electrodeposit a titanium metal film which is a metal film on the surface of the cathode. The timing of adding such titanium compound is not particularly limited, and a salt containing an alkali metal halide and a titanium compound may be mixed and then heated to form a molten salt bath, or a titanium compound may be added to a molten salt containing an alkali metal halide to form a molten salt bath.

When $K_2TiF_6$ is used as the titanium compound, the content of $K_2TiF_6$ in the molten salt bath is preferably 0.1 mol % or more. When the content of $K_2TiF_6$ is 0.1 mol % or more, the molten salt bath may be made possible to electrodeposit a titanium metal film which is a metal film on the surface of the cathode. Although the upper limit of the content of $K_2TiF_6$ in the said molten salt bath is not particularly limited, for example, it may be 10 mol % or less.

(Dissolution Step)

The dissolution step is a step of supplying titanium metal to the molten salt bath prepared in the molten salt bath preparation step as described above. The amount of titanium metal to be supplied may be at least a minimum amount required to convert $Ti^{4+}$ in the molten salt bath into $Ti^{3+}$ by a comproportionation reaction represented by the following formula (1):

$$3Ti^{4+} + Ti\ metal \rightarrow 4Ti^{3+} \qquad (1)$$

The "minimum amount" mentioned above means that the number of moles of $Ti^{4+}$ in the molten salt bath is ⅓ of the number of moles.

By dissolving a sufficient amount of titanium metal in the molten salt bath in advance, it is possible to prevent titanium metal that is electrodeposited in the subsequent electrolysis step from dissolving into the molten salt bath. Thus, according to the method for manufacturing a metal porous body according to an embodiment of the present invention, it is possible to form a smooth titanium metal film (metal film) on the surface of the framework of the porous base material which is used as the cathode.

The amount of titanium metal to be supplied to the molten salt bath is more preferably 2 times or more, and further preferably 3 times or more as many as the minimum amount mentioned in the above. Although the upper limit of the amount of titanium metal to be supplied to the molten salt bath is not particularly limited, for example, the upper limit is 120 times or less (40 times or less relative to the number of moles of $Ti^{4+}$) as many as the minimum amount mentioned in the above. In addition, for example, it is preferable that the titanium metal is supplied in such an amount that the titanium metal precipitates without completely dissolved in the molten salt bath.

Although the form of the titanium metal to be supplied is not particularly limited, it is preferable to use a titanium sponge or a titanium powder as fine as possible. In particular, a titanium sponge is preferable because it has a larger specific surface area and is more soluble in the molten salt bath. The titanium sponge preferably has a porosity of 1% to 90%. The porosity of a titanium sponge is calculated by the following formula:

100−{(the volume calculated from the mass)/(the apparent volume)×100}.

(Electrolysis Step)

The electrolysis step is a step of performing a molten salt electrolysis by using a cathode and an anode provided in the molten salt bath in which the titanium metal is dissolved. By electrolyzing the molten salt bath in which the titanium metal is dissolved, the titanium metal is electrodeposited, and thus, a titanium metal film which is a metal film may be formed on the surface of the framework of the porous base material which is used as the cathode.

[Cathode]

Figure 11:
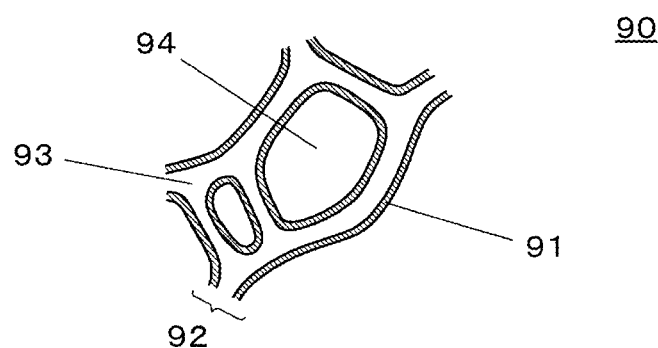
FIG. 11 is an enlarged view schematically illustrating a partial cross section of an example porous base material which has a three-dimensional network structure and is used as a cathode.
Figure 12:
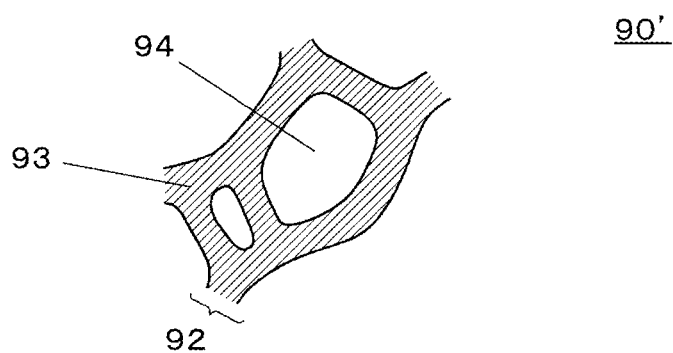
FIG. 12 is an enlarged view schematically illustrating a partial cross section of another example porous base material which has a three-dimensional network structure and is used as a cathode.

As described above, since a titanium metal film which is a metal film is formed on the surface of the cathode, a porous base material having a three-dimensional network structure (for example, a sheet-shaped porous base material having a framework of a three-dimensional network structure) (hereinafter simply referred to as "porous base material") may be used as the cathode. FIG. 11 is an enlarged view schematically illustrating a partial cross section of an example porous base material. As illustrated in FIG. 11, the framework 92 of the porous base material 90 may include at least one material 91 selected from the group consisting of a metal, an alloy, a carbon material and a conductive ceramic. Typically, the interior 93 of the frame in such as the porous base material 90 illustrated in FIG. 11 is hollow, and however, the interior of the frame in such as the porous base material 90' illustrated in FIG. 12 may not be hollow. For example, when the porous base material is formed from a metal or an alloy, the interior of the framework is often hollow. When the porous base material is formed by coating and then drying at least one material selected from the group consisting of a metal, an alloy, a carbon material and a conductive ceramic on the surface of a resin molded body (such as foamed urethane) having a framework of a three-dimensional network structure, the interior of the framework is often not hollow. In this case, since the resin molded body is removed in the treatment step described later, the interior of the framework of the final metal porous body becomes hollow. The porous base material 90 or 90' contains pores that are communicating with each other, and each pore 94 is formed by the framework 92. It is not necessary for the framework 92 per se of the porous base material 90' to have communicating pores. In other words, the framework 92 per se does not have to be porous.

When the framework 92 of the porous base material 90 or 90' is formed from a metal or an alloy, it is preferable that the metal or the alloy contains nickel, aluminum or copper as the main component. The term "main component" means that the content of nickel, aluminum or copper in the metal or alloy constituting the framework 92 is 50 mass % or more. In another aspect, the porous base material 90 or 90' may be formed from metal nickel. When the framework 92 of the porous base material 90 or 90' is formed from a metal or an alloy, at least one metal selected from the group consisting of tungsten, molybdenum, chromium and tin, or an alloy thereof may be further included.

Further, it is preferable to form a layer of tungsten or molybdenum which is hard to alloy with titanium on the surface of a metal, an alloy, a carbon material or a conductive ceramic material 91 which constitutes the framework 92 of the porous base material 90 or 90'. As a result, it is possible to produce a metal porous body with high purity, without containing titanium alloy in the titanium metal film formed on the surface of the framework 92 of the porous base material 90 or 90' in the electrolysis step.

Examples of the carbon material may include graphite and hard carbon.

Examples of the conductive ceramic may include alumina-based conductive ceramic.

As a porous base material having a three-dimensional network structure, for example, a product manufactured by Sumitomo Electric Industries, Ltd. such as Celmet (a porous metal body containing Ni as the main component, and "Celmet" is a registered trademark) or aluminum Celmet (a metal porous body containing Al as the main component, and "Aluminum Celmet" is a registered trademark) may be preferably used. In addition, any available metal porous body containing copper as the main component or any available metal or alloy to which another metal element is added may be used as the porous base material.

In addition, a layer may be formed of tungsten or molybdenum which is hard to alloy with titanium on the surface (outer surface) of the framework 92 of the porous base material 90 according to an electrolytic plating method as follows, for example.

In the case of plating tungsten on the surface of the framework of the porous base material, the electrolysis is performed in an electrolytic solution containing sodium tungstate ($Na_2WO_4$), tungsten oxide ($WO_3$) and potassium fluoride (KF) by using the porous base material as a cathode, and thereby a tungsten film may be formed on the surface of the framework of the porous base material. The molar ratio of sodium tungstate to tungsten oxide may be 1:1 to 15:1. Further, the content of potassium fluoride in the electrolytic solution may be 1 mol % or more and 20 mol % or less.

In the case of plating molybdenum on the surface of the framework of the porous base material, the electrolysis is performed in an electrolytic solution containing lithium chloride (LiCl), potassium chloride (KCl) and potassium hexachloromolybdate ($K_3MoCl_6$) by using the porous base material as a cathode, and thereby a molybdenum film may be formed on the surface of the framework of the porous base material. The content of potassium hexachloromolybdate in the electrolytic solution may be 1 mol % or more and 30 mol % or less.

Since the metal porous body is formed by electrodepositing a titanium metal film which is a metal film on the surface of the framework of the porous base material and then removing the porous base material, the porosity and the average pore diameter of the metal porous body are substantially equal to the porosity and the average pore diameter of the porous base material, respectively. Thus, the porosity and the average pore diameter of the porous base material may be appropriately selected in accordance with the porosity and the average pore diameter of the metal porous body to be produced. The porosity and the average pore diameter of the porous base material are defined in the same manner as the porosity and the average pore diameter of the metal porous body. For example, the porosity of the porous base material may be 60% or more and 96% or less, and for example, the average pore diameter of the porous base material may be 50 μm or more and 300 μm or less.

In addition, by laminating the porous base material having different average pore diameters and using the laminated body as a cathode, it is possible to produce a metal porous body wherein the average pore diameter or the apparent weight of the metal is different between a central region and an outer region located outside the central region in the thickness direction of the metal porous body. In another aspect, the porous base material may have an outer profile of a sheet shape, and the average pore diameter may be different between a region on one side and a region on the other side in the thickness direction of the sheet, or the porous base material may have an outer profile of a sheet shape, and the average pore diameter may be different between a central region and an outer region located outside the central region in the thickness direction of the sheet.

If the desired porous base material is not available in the market, it may be produced by the following method.

Figure 13:
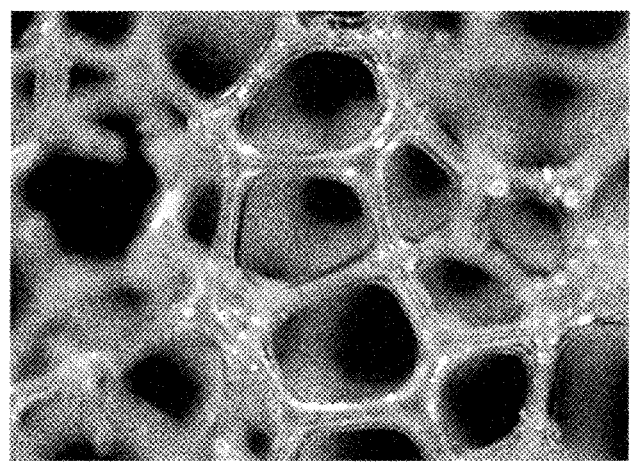
FIG. 13 is a photograph of foamed urethane resin which serves as an example of a resin molded body having a framework of a three-dimensional network structure.

First, a sheet-shaped resin molded body having a framework of a three-dimensional network structure (hereinafter, also simply referred to as a "resin molded body") is prepared. Polyurethane resin, melamine resin or the like may be used as the resin molded body. FIG. 13 is a photograph of a foamed urethane resin having a framework of a three-dimensional network structure.

Next, a conductive treatment step is performed so as to form a conductive layer on the surface of the framework of the resin molded body. The conductive treatment may be conducted by, for example, applying a conductive paint containing conductive particles such as carbon or conductive ceramic, forming a layer of a conductive metal such as nickel and copper by electroless plating, or forming a layer of a conductive metal such as aluminum by deposition or sputtering.

Subsequently, an electrolytic plating step is performed so as to electroplate a metal such as nickel, aluminum or copper by using the resin molded body with a conductive layer formed on the surface of the framework as a base material. Thus, a layer may be formed from a desired metal on the surface of the framework of the resin molded body by the electrolytic plating step. The electrolytic plating may be performed to form an alloy layer. Alternatively, a desired metal powder may be applied to the surface of the framework after the electrolytic plating step, and then subjected to heat treatment to form an alloy layer of the metal powder and the electroplated metal.

Finally, a removing step is performed by heat treatment or the like so as to remove the resin molded body that is used as the base material to provide a sheet-shaped porous base material that is made of metal or alloy and has a framework of a three-dimensional network structure.

The porosity and the average pore diameter of the porous base material are substantially equal to the porosity and the average pore diameter of the resin molded body which is used as the base material, respectively. Thus, the porosity and the average pore diameter of the resin molded body may be appropriately selected in accordance with the porosity and the average pore diameter of the porous base material to be produced. The porosity and the average pore diameter of the resin molded body are defined in the same manner as the porosity and the average pore diameter of the metal porous body.

Note that a resin molded body which has a framework of a three-dimensional network structure and the surface of the framework is subjected to a conductive treatment, or a resin molded body which is formed with a conductive metal layer (by electroless plating, sputtering or electrolytic plating) on the surface of the framework which has been subjected to a conductive treatment may be used as the porous base material directly without removing the resin molded body.

[Anode]

The anode may be made of any material as long as it is conductive, and for example, the anode may be made of glassy carbon, titanium metal or the like. From the viewpoint of stably and continuously producing titanium metal film, the anode made of Ti is preferably used.

[Current Density]

The molten salt electrolysis is preferably performed at a current density of 10 mA/cm² or more and 500 mA/cm² or less. The current density refers to the amount of electricity per apparent area of the porous base material which is used as the cathode.

By setting the current density to 10 mA/cm² or more, it is possible to prevent titanium ions from being reduced to an intermediate valence, enabling the plating to be performed efficiently. Further, by setting the current density to 500 mA/cm² or less, the diffusion of titanium ions in the molten salt bath is not a rate-limiting factor, which makes it possible to suppress the blackening of the resulting titanium metal film. From these viewpoints, the current density is more preferably 15 mA/cm² or more and 400 mA/cm² or less, further preferably 20 mA/cm² or more and 300 mA/cm² or less, and even more preferably 25 mA/cm² or more and 300 mA/cm² or less.

[Other Conditions]

The atmosphere for performing the molten salt electrolysis is not limited as long as it is a non-oxidizing atmosphere. However, even though the atmosphere is a non-oxidizing atmosphere such as nitrogen, if it reacts with titanium to cause nitrification or the like of the titanium metal film, then it is not suitable. For example, the molten salt electrolysis may be performed in a glove box that is filled or circulated with an inert gas such as argon gas.

In the electrolysis step, the temperature of the molten salt bath is preferably 650° C. or more and 850° C. or less. When the temperature of the molten salt bath is 650° C. or more, the molten salt bath is maintained in a liquid state, enabling the molten salt electrolysis to be performed stably. When the temperature of the molten salt bath is 850° C. or less, the molten salt bath may be prevented from becoming unstable due to the evaporation of the components of the molten salt bath. From these viewpoints, the temperature of the molten salt bath is more preferably 650° C. or more and 750° C. or less, and further preferably 650° C. or more and 700° C. or less.

The length of time for the molten salt electrolysis is not particularly limited, and it may be any length of time that is sufficient to form a target titanium metal film.

After the electrolysis step, the porous base material on which the metal film is formed may be washed with water so as to remove salts or the like adhered to the surface of the metal film.

(Treatment Step)

The treatment step is a step of treating the cathode on which the titanium is electrodeposited with an acid or an alkali. After the treatment step, the porous base that is used as the cathode can be removed, providing a metal porous body including a framework which has a three-dimensional network structure and is hollow inside. The treatment process may be performed after the cathode is removed from the molten salt electrolysis apparatus.

The method for treating the cathode with an acid or an alkali is not particularly limited, and the cathode may be simply immersed in an acidic or alkaline solution. When the cathode is being immersed in an acidic or alkaline solution, since the framework of the porous base material which is used as the cathode is hollow inside, the acidic or alkaline solution is infiltrated into the framework by capillary action. As a result, the surface of the hollow interior of the framework of the porous base material comes into contact with the acidic or alkaline solution, and is dissolved and removed by the same.

As described above, the porous base material formed with the titanium metal film on the surface of the framework may be simply immersed in an acidic or alkaline solution, but the porous base material may be removed more efficiently by stirring the acidic or alkaline solution. The stirring is not particularly limited, it may be performed by using a magnetic stirrer, or it may be performed by using ultrasonic waves. If the stirring is performed by using ultrasonic waves, the ultrasonic wave applied to the acidic or alkaline solution may have a frequency of about 37 kHz.

Moreover, it is preferable that the treatment step is performed at a temperature of 20° C. or more. If the treatment step is performed by setting the temperature of the acidic or alkaline solution to 20° C. or more, the porous base material is easy to be dissolved, which facilitates the removal of the porous base material.

The acid or base is not limited, it may be any acid or base that will not dissolve titanium but can dissolve the metal, alloy, carbon material or conductive ceramic constituting the porous base material. For example, hydrochloric acid (HCl), sulfuric acid ($H_2SO_4$), sodium hydroxide (NaOH), dilute nitric acid ($HNO_3$) or the like may be used.

The concentration and the treatment time of the acid or alkali to be used may vary depending on treatment conditions such as the type and the stirring of the acid or alkali, and may be adjusted appropriately so as to satisfactorily remove the porous base material which is used as the cathode. For example, if the porous base material is made of nickel, and hydrochloric acid is used to remove the porous base material and the stirring is performed by ultrasonic irradiation at a frequency of about 37 kHz, the porous base material may be immersed in hydrochloric acid with a concentration of about 12 mass % for about 5 minutes.

Furthermore, when it is desired to more clearly remove the dissolution residue of the porous base material, the porous base material may be more efficiently dissolved through positive polarization in the acid or alkali. At this time, since titanium metal or titanium alloy is high in voltage resistance, it will not be dissolved.

In addition, it is preferable that the porous base material having the titanium metal film formed on the surface of the framework is hydrophilized with a surfactant before it is treated with an acid or an alkali. As a result, the interior of the framework of the porous base material is improved in wettability to the acidic or alkaline aqueous solution, enabling the treatment to be performed efficiently. The surfactant is not particularly limited, and as an example, sodium stearate, sodium alkylbenzene sulfonate or the like may be given. In addition, the alkyl group of sodium alkylbenzene sulfonate may be methyl, ethyl or the like.

<Method for Producing Hydrogen, and Hydrogen Producing Apparatus>

The metal porous body according to an embodiment of the present invention may be suitably used, for example, as a fuel-cell electrode (for example, an electrode for a polymer electrolyte fuel cell) and an electrode used in the production of hydrogen by water electrolysis (for example, an insoluble positive electrode). The method for producing hydrogen are roughly classified into [1] alkaline water electrolysis system and [2] PEM (Polymer Electrolyte Membrane) system, and the metal porous body may be suitably used in each system.

In the alkaline water electrolysis system [1], the positive electrode and the negative electrode are immersed in a strong alkaline aqueous solution, and water is electrolyzed by applying voltage. When the metal porous body is used as the electrode, the contact area between water and the electrode is increased, which makes it possible to improve the efficiency of the water electrolysis.

In the method for producing hydrogen by the alkaline water electrolysis system, the average pore diameter of the metal porous body is preferably 100 μm or more and 5000 μm or less when viewed from the above (for example, when viewed from the main surface of the sheet-shaped metal porous body). If the average pore diameter of the metal porous body when viewed from the above is 100 μm or more, it is possible to restrain the contact area between water and the electrode from decreasing due to the reason that the generated hydrogen and oxygen bubbles are clogged in the pores of the metal porous body. On the other hand, if the average pore diameter of the metal porous body when viewed from the above is 5000 μm or less, the surface area of the electrode becomes sufficiently large, which makes it possible to improve the efficiency of water electrolysis. From the same viewpoints, the average pore diameter of the metal porous body when viewed from the above is more preferably 400 μm or more and 4000 μm or less.

The thickness of the metal porous body and the apparent weight of the metal may cause deflection when the electrode area becomes large, so that the thickness and the apparent weight of the metal may be appropriately selected according to the scale of equipment. The apparent weight of the metal is preferably about 200 $g/m^2$ or more and 2000 $g/m^2$ or less, more preferably about 300 $g/m^2$ or more and 1200 $g/m^2$ or less, and further preferably about 400 $g/m^2$ or more and 1000 $g/m^2$ or less. In order to ensure the balance between the escape of bubbles and the surface area, a plurality of metal porous bodies having different average pore diameters may be used in combination.

The PEM system [2] is configured to electrolyze water by using a solid polymer electrolyte membrane. The positive electrode and the negative electrode are placed at both sides of the solid polymer electrolyte membrane, and a voltage is applied while water is being introduced to the positive electrode side to perform the water electrolysis; and hydrogen ions generated by the water electrolysis are transferred to the negative electrode side through the solid polymer electrolyte membrane, and are taken out as hydrogen from the negative electrode side. In other words, in the PEM system [2], the metal porous bodies are disposed at both sides of the solid polymer electrolyte membrane and brought into contact with the solid polymer electrolyte membrane so that the metal porous bodies act as a positive electrode and a negative electrode, respectively, to electrolyze water supplied to the positive electrode side, and thereby hydrogen is generated at the negative electrode side and taken out therefrom. The operating temperature is about 100° C. This system has the same configuration but operates completely different from a polymer electrolyte fuel cell that generates electric power by using hydrogen and oxygen and discharges the generated water to the outside. Because the positive electrode side and the negative electrode side are completely separated from each other, there is an advantage that high purity hydrogen can be taken out. Since water and hydrogen gas are needed to pass through both the positive electrode and the negative electrode, it is required that the electrodes are made of a conductive porous material.

Since the metal porous body according to an embodiment of the present invention has high porosity and excellent electrical conductivity, it may be suitably used not only in the polymer electrolyte fuel cell but also in the water electrolysis by the PEM system. In the method for producing hydrogen by the PEM system, the average pore diameter of the metal porous body when viewed from the above is preferably 150 μm or more and 1000 μm or less. If the average pore diameter of the metal porous body when viewed from the above is 150 μm or more, it is possible to restrain the contact area between water and the electrode from decreasing due to the reason that the generated hydrogen and oxygen bubbles are clogged in the pores of the metal porous body. On the other hand, if the average pore diameter of the metal porous body when viewed from the above is 1000 μm or less, it is possible to ensure sufficient water retention so as to prevent water from passing through before getting involved in reaction, enabling the water electrolysis to be performed efficiently. From the same viewpoints, the average pore diameter of the metal porous body when viewed from the above is more preferably 200 μm or more and 700 μm or less, and further preferably 300 μm or more and 600 μm or less.

The thickness of the metal porous body and the apparent weight of the metal may be appropriately selected according to the scale of equipment. However, if the porosity is too small, the loss of a pressure which urges water to pass through the metal porous body may become large, and thus, it is preferable to adjust the thickness and the apparent weight of the metal such that the porosity is 30% or more. In the PEM system, since the conductive connection between the solid polymer electrolyte membrane and the electrode is established by pressure bonding, it is necessary to adjust the apparent weight of the metal such that an increase in electrical resistance due to the deformation and creep resulted from the pressure bonding falls within a practically acceptable range. The apparent weight of the metal is preferably about 200 g/m$^2$ or more and 2000 g/m$^2$ or less, more preferably about 300 g/m$^2$ or more and 1200 g/m$^2$ or less, and further preferably about 400 g/m$^2$ or more and 1000 g/m$^2$ or less. Further, in order to ensure the balance between the porosity and the electrical connection, a plurality of metal porous bodies having different average pore diameters may be used in combination.

The hydrogen producing apparatus according to the present embodiment is an hydrogen producing apparatus that is configured to generate hydrogen by electrolyzing water, and includes the metal porous body mentioned above as an electrode. In addition to the electrode, the hydrogen producing apparatus may further include an ion exchange membrane, a power supply device, an electrolytic cell, and an electrolytic solution containing water, for example. In another aspect, the water used in the hydrogen producing apparatus is preferably a strong alkaline aqueous solution.

In another aspect, the hydrogen producing apparatus includes a positive electrode and a negative electrode disposed at both sides of a solid polymer electrolyte membrane and configured to be in contact with the solid polymer electrolyte membrane, the hydrogen producing apparatus is configured to electrolyze water supplied to the positive electrode side so as to generate hydrogen at the negative electrode side, and at least one of the positive electrode and the negative electrode is preferably made of the metal porous body.

<Biomaterial and Medical Device Including the Same>

The biomaterial according to the present embodiment is made of the metal porous body mentioned above. The metal porous body mentioned above is excellent in corrosion resistance, and thereby may be suitably used as a biomaterial. The medical device according to the present embodiment contains the biomaterial. The medical device is preferably selected from the group consisting of a spinal fixation device, a fracture fixation member, an artificial joint, an artificial valve, an intravascular stent, a dental plate, an artificial tooth root and an orthodontic wire.

<Notes>

The above description includes the features noted below.

(Note 1)

A method for producing hydrogen by electrolyzing water using a metal porous body having a framework of a three-dimensional network structure as an electrode, the framework is hollow inside, and the framework contains titanium metal or titanium alloy as the main component.

(Note 2)

The method for producing hydrogen according to Note 1, wherein the average thickness of the framework is 1 μm or more and 300 μm or less.

(Note 3)

The method for producing hydrogen according to Note 1 or 2, wherein the porosity of the metal porous body is 60% or more and 98% or less.

(Note 4)

The method for producing hydrogen according to any one of Notes 1 to 3, wherein the average pore diameter of the metal porous body is 50 μm or more and 500 μm or less.

(Note 5)

The method for producing hydrogen according to any one of Notes 1 to 3, wherein the average pore diameter of the metal porous body is different between a region above the center line and a region below the center line in the thickness direction of the metal porous body.

(Note 6)

The method for producing hydrogen according to any one of Notes 1 to 3 and 5, wherein the apparent weight of the metal porous body is different between a region above the center line and a region below the center line in the thickness direction of the metal porous body.

(Note 7)

The method for producing hydrogen according to any one of Notes 1 to 3, wherein the average pore diameter of the metal porous body is different between a central region and an outer region located outside the central region in the thickness direction of the metal porous body.

(Note 8)

The method for producing hydrogen according to any one of Notes 1 to 3 and 7, wherein the apparent weight of the metal porous body is different between a central region and an outer region located outside the central region in the thickness direction of the metal porous body.

(Note 9)

The method for producing hydrogen according to any one of Notes 1 to 8, wherein the water is a strong alkaline aqueous solution.

(Note 10)

The method for producing hydrogen according to any one of Notes 1 to 9, wherein the metal porous bodies are disposed at both sides of a solid polymer electrolyte membrane and brought into contact with the solid polymer electrolyte membrane so that the metal porous bodies act as a positive electrode and a negative electrode, respectively, to electrolyze water supplied to the positive electrode side so as to generate hydrogen at the negative electrode side.

(Note 12)

An hydrogen producing apparatus configured to generate hydrogen by electrolyzing water, the hydrogen producing apparatus includes a metal porous body having a framework of a three-dimensional network structure as an electrode, the framework is hollow inside, and the framework contains titanium metal or titanium alloy as the main component.

(Note 13)

The hydrogen producing apparatus according to Note 12, wherein the average thickness of the framework is 1 µm or more and 300 µm or less.

(Note 14)

The hydrogen producing apparatus according to Note 12 or 13, wherein the porosity of the metal porous body is 60% or more and 98% or less.

(Note 15)

The hydrogen producing apparatus according to any one of Notes 12 to 14, wherein the average pore diameter of the metal porous body is 50 µm to 500 µm.

(Note 16)

The hydrogen producing apparatus according to any one of Notes 12 to 14, wherein the average pore diameter of the metal porous body is different between a region above the center line and a region below the center line in the thickness direction of the metal porous body.

(Note 17)

The hydrogen producing apparatus according to any one of Notes 12 to 14 and 16, wherein the apparent weight of the metal porous body is different between a region above the center line and a region below the center line in the thickness direction of the metal porous body.

(Note 18)

The hydrogen producing apparatus according to any one of Notes 12 to 14, wherein the average pore diameter of the metal porous body is different between a central region and an outer region located outside the central region in the thickness direction of the metal porous body.

(Note 19)

The hydrogen producing apparatus according to any one of Notes 12 to 14 and 18, wherein the apparent weight of the metal porous body is different between a central region and an outer region located outside the central region in the thickness direction of the metal porous body.

(Note 20)

The hydrogen producing apparatus according to any one of Notes 12 to 19, wherein the water is a strong alkaline aqueous solution.

(Note 21)

The hydrogen producing apparatus according to any one of Notes 12 to 20, wherein the hydrogen producing apparatus includes a positive electrode and a negative electrode disposed at both sides of a solid polymer electrolyte membrane and configured to be in contact with the solid polymer electrolyte membrane, the hydrogen producing apparatus is configured to electrolyze water supplied to the positive electrode side so as to generate hydrogen at the negative electrode side, and at least one of the positive electrode and the negative electrode is made of the metal porous body.

(Note 101)

A metal porous body having a framework of a three-dimensional network structure, the framework is hollow inside, and the framework contains titanium metal or titanium alloy as the main component.

(Note 102)

The metal porous body according to Note 101, wherein the average thickness of the framework is 1 µm or more and 300 µm or less.

(Note 103)

The metal porous body according to Note 101 or 102, wherein the porosity of the metal porous body is 60% or more and 98% or less.

(Note 104)

The metal porous body according to any one of Notes 101 to 103, wherein the average pore diameter of the metal porous body is 50 µm or more and 5000 µm or less.

(Note 105)

The metal porous body according to any one of Notes 101 to 103, wherein the average pore diameter of the metal porous body is different between a region above the center line and a region below the center line in the thickness direction of the metal porous body.

(Note 106)

The metal porous body according to any one of Notes 101 to 103 and 105, wherein the apparent weight of the metal porous body is different between a region above the center line and a region below the center line in the thickness direction of the metal porous body.

(Note 107)

The metal porous body according to any one of Notes 101 to 103, wherein the average pore diameter of the metal porous body is different between a central region and an outer region located outside the central region in the thickness direction of the metal porous body.

(Note 108)

The metal porous body according to any one of Notes 101 to 103 and 107, wherein the apparent weight of the metal porous body is different between a central region and an outer region located outside the central region in the thickness direction of the metal porous body.

(Note 109)

A method for producing the metal porous body according to Note 101, includes:

a molten salt bath preparation step of preparing a molten salt bath that contains an alkali metal halide and a titanium compound;

a dissolution step of dissolving titanium metal in the molten salt bath;

an electrolysis step of performing a molten salt electrolysis by using a cathode and an anode provided in the molten salt bath in which the titanium metal is dissolved so as to electrodeposit the titanium metal on the surface of the cathode; and a treatment step of treating the cathode on which the titanium metal is electrodeposited with an acid or an alkali, in the dissolution step, the titanium metal is supplied in at least a minimum amount required to convert $Ti^{4+}$ in the molten salt bath into $Ti^{3+}$ by a comproportionation reaction represented by the following formula (1):

$$3Ti^{4+} + Ti\ metal \rightarrow 4Ti^{3+} \qquad (1),$$

in the electrolysis step, a porous base material which has a three-dimensional network structure is used as the cathode.

(Note 110)

The method for producing a metal porous body according to Note 109, wherein the porous base material includes at least one material selected from the group consisting of a metal, an alloy, a carbon material and a conductive ceramic.

(Note 111)

The method for producing a metal porous body according to Note 109 or 110, wherein the treatment step is performed at a temperature of 20° C. or more.

(Note 112)

The method for producing a metal porous body according to any one of Notes 109 to 111, wherein the porous base material used as the cathode is formed by laminating the porous body base bodies having different average pore diameters.

(Note 113)

The method for producing a metal porous body according to any one of Notes 109 to 112, wherein the titanium to be dissolved in the dissolution step is a titanium sponge.

(Note 114)

The method for producing a metal porous body according to any one of Notes 109 to 113, wherein titanium is used as the anode.

EXAMPLES

Hereinafter, the present disclosure will be described in more detail with reference to examples. The examples are by way of illustration only, and the metal porous body of the present disclosure and the method for producing the same are not limited to the examples. The scope of the present disclosure is defined by the scope of the claims and encompasses all modifications equivalent in meaning and scope to the claims.

Example

—Molten Salt Bath Preparation Step—

KCl, KF and $K_2TiF_6$ were mixed in such a manner that the molar mixing ratio of KCl and KF is 55:45 and the concentration of $K_2TiF_6$ is 0.1 mol %, and the mixture was heated to 650° C. to prepare a molten salt bath.

—Dissolution Step—

To the molten salt bath prepared in the molten salt bath preparation step described above, 13 mg of a titanium sponge per 1 g of the molten salt bath (an amount equivalent to 40 times the number of moles of $Ti^{4+}$ in the molten salt bath) was added, and sufficiently dissolved therein. The titanium sponge was not completely dissolved in the molten salt bath and precipitated partially.

—Electrolysis Step—

The molten salt electrolysis was performed in a glove box under an Ar flow atmosphere.

As a porous base material to be used as a cathode, a porous base material which is made of nickel and has a framework of a three-dimensional network structure (hereinafter referred to as "nickel porous body") was prepared. The porosity of the nickel porous body was 96%, and the average pore diameter thereof was 300 μm. This nickel porous body was processed into 3 cm×5 cm×1 mmt and used as a cathode.

A Ti bar was used as the anode, and a Pt wire was used as a pseudo reference electrode.

Then, a voltage was applied to the cathode and the anode so that the current density was 25 mA/cm² to perform the molten salt electrolysis. The potential of the pseudo reference electrode was calibrated by the potential of metal K electrochemically deposited on the Pt wire ($K^+$/K potential).

As a result, a titanium metal film, which is a metal film, was formed on the surface of the framework of the nickel porous body used as the cathode.

—Water Washing—

After the electrolysis step, the nickel porous body formed with a titanium metal film on the surface of the framework of the nickel porous body was washed with water. The salt adhered to the surface of the titanium metal film was highly soluble in water and was easily removed.

—Treatment Step—

After the water washing step, the porous nickel body formed with a titanium metal film on the surface of the framework was immersed in 20 mass % $HNO_3$ for 120 minutes.

As a result, the nickel porous body was removed, and a metal porous body No. 1 which has a framework of a three-dimensional network structure and the framework is hollow inside was obtained.

Comparative Example

A titanium plate No. A was prepared in the same manner as Example except that a nickel plate of 3 cm×5 cm×1 mmt was used as the cathode in the electrolysis step.

—Evaluation—

The metal porous body No. 1 prepared in Example had a porosity of 96% and an average pore diameter of 280 μm. The titanium metal film of the metal porous body No. 1 had an average film thickness of 15 μm. In the cross section of the framework of the metal porous body No. 1, an alloy layer was formed on the surface facing the interior of the framework. The alloy layer thus formed includes a composite layer of $TiNi_3$ and Ni, a composite layer of TiNi and $TiNi_3$, and a composite layer of $Ti_2Ni$ and TiNi in the order from the side facing the interior of the framework. The thickness of the alloy layer was about 3 μm.

For the titanium plate No. A prepared in Comparative Example, the average film thickness of the titanium metal film was 110 μm. Note that the average film thickness of the titanium metal film constituting the titanium plate No. A was calculated by measuring the maximum thickness and the minimum thickness of the titanium metal film in the cross section of area A to area E of the titanium plate instead of measuring the maximum thickness and the minimum thickness of the titanium metal film 11 in the A-A cross section of the framework according to the above-mentioned method for measuring the average film thickness of the titanium metal film of the metal porous body.

As mentioned above, the average film thickness of the titanium metal film of the metal porous body No. 1 was ⅛ of that of the titanium metal film of the titanium plate No. A. Since the plating of titanium was conducted with the same amount of electricity in Example and Comparative Example, it was obvious that the surface area of the metal porous body No. 1 is about 8 times as large as that of the titanium plate No. A.

(Corrosion Resistance to Saline)

The corrosion resistance of a test specimen (Ti-plated product) of Example to saline was performed in the following procedure.

<Preparation of Test Specimen>

The test specimen of Example was prepared in the same manner as that described above in the (Example) section. As the test specimens of Comparative Example, a Ni porous body (manufactured by Sumitomo Electric Industries, Ltd., trade name: Celmet (registered trademark)) and a Ti metal sheet (manufactured by Nilako Corporation) were used.

<Corrosion Resistance Test>

Figure 14:
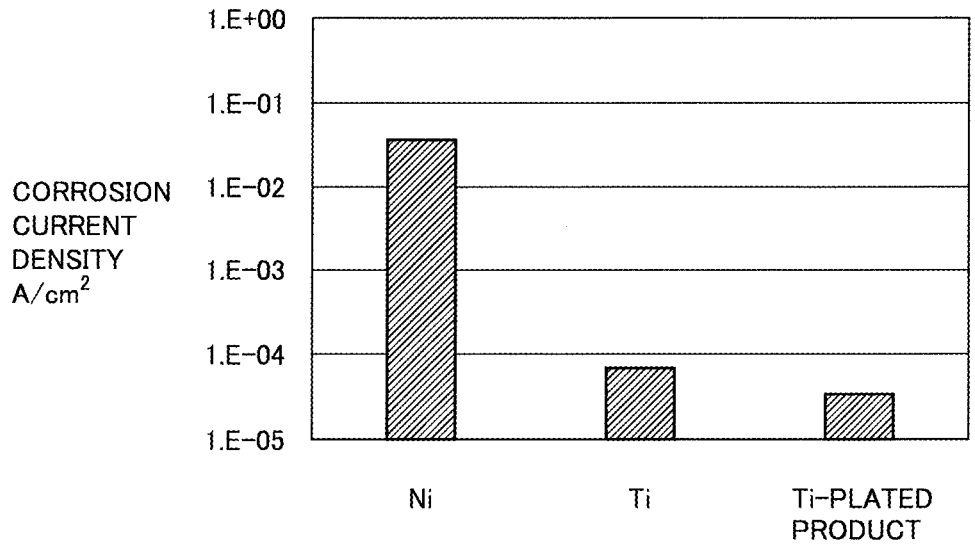
FIG. 14 is a graph illustrating corrosion current density of each electrode in saline.

Cyclic voltammetry was performed under the following conditions. The results are shown in FIG. 14. In FIG. 14, the test specimen of Example and the test specimens of Comparative Example (the Ni porous body and the Ti metal sheet) are denoted as "Ti-plated product", "Ni" and "Ti", respectively.

Conditions of Cyclic Voltammetry

Electrolyte: 0.9 mass % sodium chloride aqueous solution (saline)

Working electrode: test specimen of Example or test specimen of Comparative Example (the Ni porous body or the Ti metal sheet)

Reference electrode: Ag/AgCl electrode

Counter electrode: Ni metal sheet

Scanning speed: 10 mV/sec

Liquid temperature: 25° C.

From the results of FIG. 14, it was found that the Ti-plated product of Example has a lower corrosion current density as compared with the Ni porous body of Comparative Example, and thus it is more stable in saline. Therefore, the Ti-plated product of Example (the metal porous body of the present embodiment) is suitable as a biomaterial. Moreover, as compared with the Ti metal sheet of Comparative Example, it was found that the Ti-plated product, which is a metal porous body, has a lower corrosion current density. Therefore, when the metal porous body is used instead of the metal sheet, it would be more stable in saline.

(Corrosion Resistance to Salt Solution)

The corrosion resistance of a Ti-plated product of Example to a salt solution was evaluated by the following procedure.

<Preparation of Test Specimen>

The test specimen of Example was prepared in the same manner as that described above in the (Example) section. As the test specimen of Comparative Example, a Ti metal sheet (manufactured by Nilako Corporation) was used.

<Corrosion Resistance Test>

Cyclic voltammetry was performed under the same conditions as those described above in the (Corrosion Resistance to Saline) section except that 3.3 mass % salt solution that simulates seawater was used as the electrolytic solution.

Figure 15:
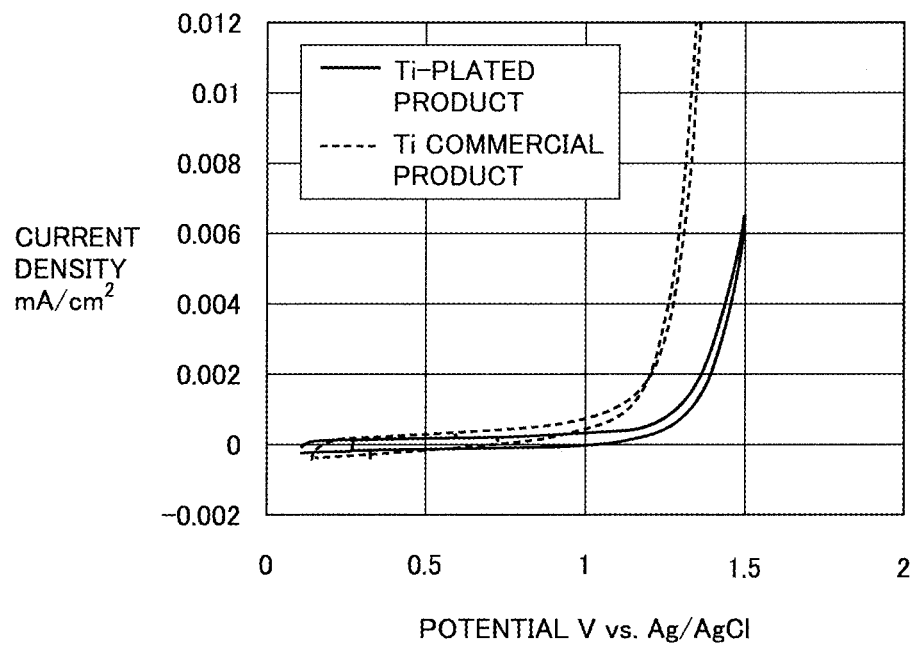
FIG. 15 is a graph illustrating the correlation between the current density and the potential of each electrode in simulated seawater.

The results are shown in FIG. 15. In FIG. 15, the test specimen of Example and the test specimen of Comparative Example are denoted as "Ti-plated product" and "Ti commercial product", respectively.

From the results of FIG. 15, it was found that the Ti-plated product of Example has a lower current density as compared with the Ti commercial product of Comparative Example, and thereby, it has a higher corrosion resistance to seawater. Therefore, the Ti-plated product of Example (the metal porous body of the present embodiment) is promising as an insoluble positive electrode for sodium chloride electrolysis.

(Evaluation of Suitability for Polymer Electrolyte Fuel Cell)

The suitability of the Ti-plated product of Example for a polymer electrolyte fuel cell was evaluated according to the following procedure.

<Preparation of Test Specimen>

The test specimen of Example was prepared in the same manner as that described above in the (Example) section. As the test specimens of Comparative Example, a Ni porous body (manufactured by Sumitomo Electric Industries, Ltd., trade name: Celmet (registered trademark)) and a Ti metal sheet (manufactured by Nilako Corporation) were used.

<Evaluation of Suitability>

Figure 16A:
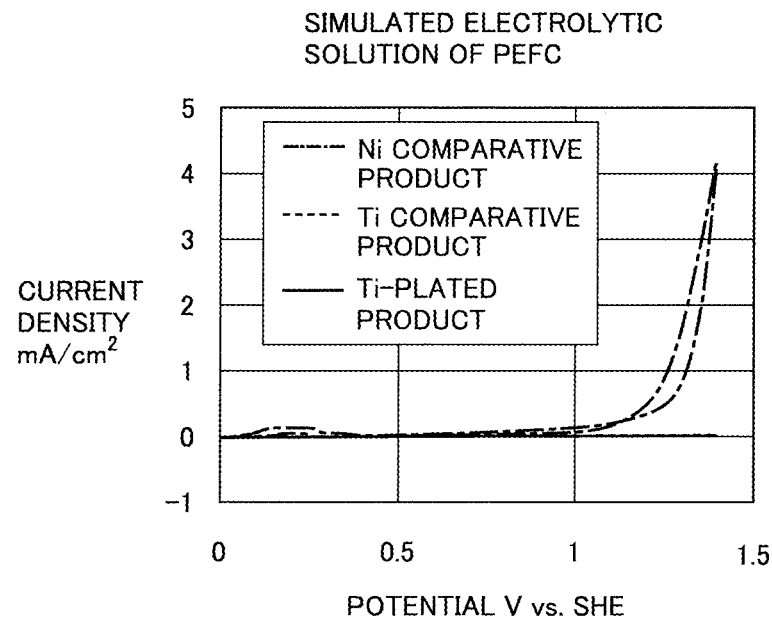
FIG. 16A is a graph illustrating the correlation between the current density and the potential of each electrode in a simulated electrolytic solution of a polymer electrolyte fuel cell (PEFC)
Figure 16B:
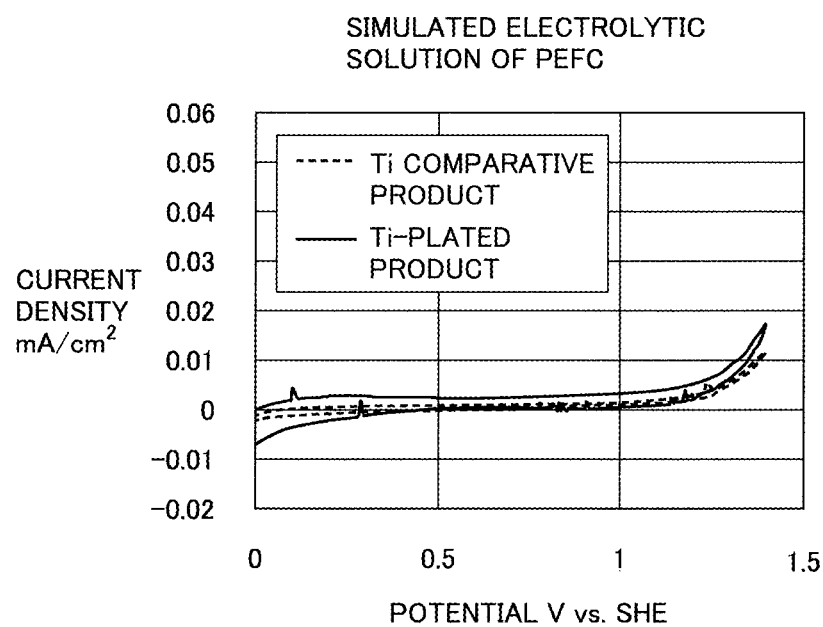
FIG. 16B is a graph illustrating the correlation between the current density and the potential of each electrode in a simulated electrolytic solution of a polymer electrolyte fuel cell (PEFC).

Cyclic voltammetry was performed under the same conditions as those described above in the (Corrosion Resistance to Saline) section except that 10 mass % sodium sulfate aqueous solution (sulfuric acid was added to adjust pH to 3) (PEFC simulated electrolytic solution) was used as the electrolytic solution. The results are shown in FIG. 16A and FIG. 16B. In FIG. 16A and FIG. 16B, the test specimen of Example and the test specimens of Comparative Example (the Ni porous body of and the Ti metal sheet) are denoted as "Ti-plated product", "Ni comparative product" and "Ti comparative product", respectively.

From the results of FIG. 16A and FIG. 16B, it was found that the Ti-plated product of Example (the metal porous body of the present embodiment) has a lower current density as compared with the Ni comparative product of Comparative Example, and thereby it is promising as an electrode material for use in polymer electrolyte fuel cells.

REFERENCE SIGNS LIST

10: metal porous body; 11: metal film (titanium metal film); 12: framework; 13: interior; 14: pore; 20: metal porous body; 30: metal porous body; 40: metal porous body; 50: metal porous body; 90: porous base material; 90': porous base material; 91: at least one material selected from the group consisting of a metal, an alloy, a carbon material and a conductive ceramic; 92: framework; 93: interior; 94: pore

The invention claimed is:

1. A metal porous body having a framework of a three-dimensional network structure,
   the framework formed of a metal film and the framework having an interior that is hollow, wherein the metal film has an average thickness of 1 μm or more and 300 μm or less,
   the metal film containing titanium metal or titanium alloy, a content of the titanium metal or the titanium alloy of the metal film being 90 mass % or more,
   the metal porous body has a sheet shape, the sheet shape having a predetermined length in a length direction, a predetermined width in a width direction, and a predetermined thickness in a thickness direction,
   the sheet shape is divided into at least two regions in the thickness direction of the sheet shape, the at least two regions composed of the titanium metal or the titanium alloy of the metal film, the content of the at least two regions composed of the titanium metal or the titanium alloy of the metal film being 90 mass % or more, a boundary separates each of the at least two regions in the thickness direction of the sheet shape, and one or both of an average pore diameter of the metal porous body and a weight of the metal porous body is different between the at least two regions, the weight being a mass per unit area.

2. The metal porous body according to claim 1, wherein the metal porous body has a porosity of 60% or more and 98% or less.

3. The metal porous body according to claim 1, wherein the metal porous body has an average pore diameter of 50 µm or more and 5000 µm or less.

4. The metal porous body according to claim 1, wherein the average pore diameter of the metal porous body is different between a first region of the at least two regions on a first side and a second region of the at least two regions on a second side in the thickness direction of the sheet shape.

5. The metal porous body according to claim 1 wherein the weight of the metal porous body is different between a first region of the at least two regions on a first side and a second region of the at least two regions on a second side in the thickness direction of the sheet shape.

6. The metal porous body according to claim 1, wherein the average pore diameter of the metal porous body is different between a central region of the at least two regions and outer regions of the at least two regions located outside the central region in the thickness direction of the sheet shape.

7. The metal porous body according to claim 1, wherein the weight of the metal porous body is different between a central region of the at least two regions and outer regions of the at least two regions located outside the central region in the thickness direction of the sheet shape.

8. A method for producing a metal porous body according to claim 1, comprising:

a molten salt bath preparation step of preparing a molten salt bath that contains an alkali metal halide and a titanium compound;

a dissolution step of dissolving titanium metal in the molten salt bath;

an electrolysis step of performing a molten salt electrolysis by using a cathode and an anode provided in the molten salt bath in which the titanium metal is dissolved so as to electrodeposit the titanium metal on the surface of the cathode; and a treatment step of treating the cathode on which the titanium metal is electrodeposited with an acid or an alkali, in the dissolution step, the titanium metal being supplied in at least a minimum amount required to convert $Ti^{4+}$ in the molten salt bath into $Ti^{3+}$ by a comproportionation reaction represented by the following formula (1):

$$3Ti^{4+} + Ti\ metal \rightarrow 4Ti^{3+} \qquad (1),$$

in the electrolysis step, a porous base material which has a three-dimensional network structure being used as the cathode.

9. The method for producing a metal porous body according to claim 8, wherein the porous base material includes at least one material selected from the group consisting of a metal, an alloy, a carbon material and a conductive ceramic.

10. The method for producing a metal porous body according to claim 8, wherein the treatment step is performed at a temperature of 20° C. or more.

11. The method for producing a metal porous body according to claim 8, wherein the porous base material used as the cathode has an outer profile of a sheet shape, and the average pore diameter is different between a region on one side and a region on the other side in the thickness direction of the sheet, or the porous base material used as the cathode has an outer profile of a sheet shape, and the average pore diameter is different between a central region and an outer region located outside the central region in the thickness direction of the sheet.

12. The method for producing a metal porous body according to claim 8, wherein the titanium metal to be dissolved in the dissolution step is a titanium sponge.

13. The method for producing a metal porous body according to claim 8, wherein the titanium metal is used as the anode.

14. An insoluble positive electrode made of the metal porous body according to claim 1.

15. The insoluble positive electrode according to claim 14, wherein the insoluble positive electrode is used in the production of hydrogen.

16. A fuel-cell electrode made of the metal porous body according to claim 1.

17. The fuel-cell electrode according to claim 16, wherein the fuel-cell electrode is used in a polymer electrolyte fuel cell.

18. A method for producing hydrogen in which hydrogen is generated by electrolyzing water using the metal porous body according to claim 1 as an electrode.

19. The method for producing hydrogen according to claim 18, wherein the water is an alkaline aqueous solution.

20. The method for producing hydrogen according to claim 18, wherein the metal porous bodies are disposed at both sides of a solid polymer electrolyte membrane and brought into contact with the solid polymer electrolyte membrane so that the metal porous bodies act as a positive electrode and a negative electrode, respectively, to electrolyze water supplied to the positive electrode side so as to generate hydrogen at the negative electrode side.

21. A hydrogen producing apparatus configured to generate hydrogen by electrolyzing water, comprising the metal porous body according to claim 1 as an electrode.

22. The hydrogen producing apparatus according to claim 21, wherein the water is a strong alkaline aqueous solution.

23. The hydrogen producing apparatus according to claim 21, wherein the hydrogen producing apparatus includes a positive electrode and a negative electrode disposed at both sides of a solid polymer electrolyte membrane and configured to be in contact with the solid polymer electrolyte membrane, the hydrogen producing apparatus is configured to electrolyze water supplied to the positive electrode side so as to generate hydrogen at the negative electrode side, and at least one of the positive electrode and the negative electrode is made of the metal porous body.

24. A biomaterial made of the metal porous body according to claim 1.

25. A medical device comprising the biomaterial according to claim 24.

26. The medical device according to claim 25, wherein the medical device is selected from the group consisting of a spinal fixation device, a fracture fixation member, an artificial joint, an artificial valve, an intravascular stent, a dental plate, an artificial tooth root and an orthodontic wire.

* * * * *